United States Patent [19]
Smith et al.

[11] Patent Number: 5,661,227
[45] Date of Patent: Aug. 26, 1997

[54] MOISTURE SENSOR FOR MICROWAVE CLOTHES DRYER

[75] Inventors: Richard D. Smith, Palo Alto; Ronald R. Lentz, Modesto; Patrick C. Meachim, Oakdale, all of Calif.

[73] Assignee: Electric Power Research Institute, Palo Alto, Calif.

[21] Appl. No.: 557,846

[22] Filed: Nov. 14, 1995

[51] Int. Cl.$^6$ .................... G01R 27/00; G01N 35/00
[52] U.S. Cl. .................... 73/29.01; 73/335.05; 73/73; 324/694; 324/696; 34/528; 34/550; 34/260
[58] Field of Search .................... 73/29.01, 29.02, 73/335.05, 73; 324/693, 694, 696, 703, 722, 724; 34/260, 528, 550

[56] References Cited

U.S. PATENT DOCUMENTS

| | | | |
|---|---|---|---|
| 3,005,154 | 10/1961 | Moore et al. | 324/694 |
| 3,221,417 | 12/1965 | Mellinger | 34/528 |
| 3,222,798 | 12/1965 | Thornbery et al. | 34/528 |
| 3,243,891 | 4/1966 | Smith | 34/528 |
| 3,284,918 | 11/1966 | Malecki et al. | 34/528 X |
| 3,613,253 | 10/1971 | Smith | 324/696 X |
| 3,613,254 | 10/1971 | Smith | 324/696 X |
| 3,824,476 | 7/1974 | Cotton | 34/528 X |
| 4,451,781 | 5/1984 | Anderson | 324/694 |
| 5,396,715 | 3/1995 | Smith | 34/261 |

FOREIGN PATENT DOCUMENTS

| 81442 | 7/1981 | Japan | 324/694 |
|---|---|---|---|

*Primary Examiner*—Hezron E. Williams
*Assistant Examiner*—Daniel S. Larkin
*Attorney, Agent, or Firm*—Flehr, Hohbach, Test, Albritton & Herbert

[57] ABSTRACT

Microwave clothes dryer with a moisture sensor having an array of short coaxial cables extending through an electrically conductive base plate which is grounded to the shielding structure of the dryer. The ends of the cables are flush with one side of the plate and are exposed for contact with clothes in the dryer chamber. Electrical resistance is monitored between the inner conductors and the plate to determine the dryness of clothes, and the dryer is shut down when the resistance reaches a predetermined level.

10 Claims, 1 Drawing Sheet

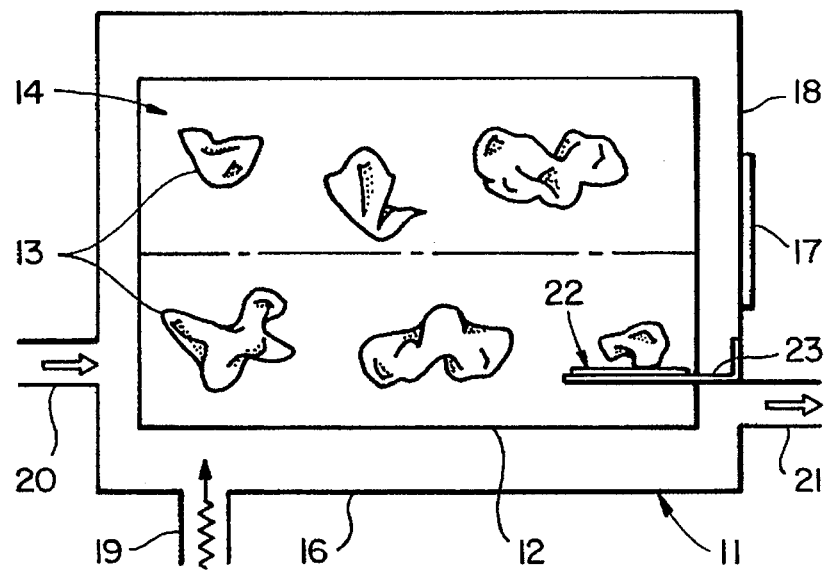
FIG_1
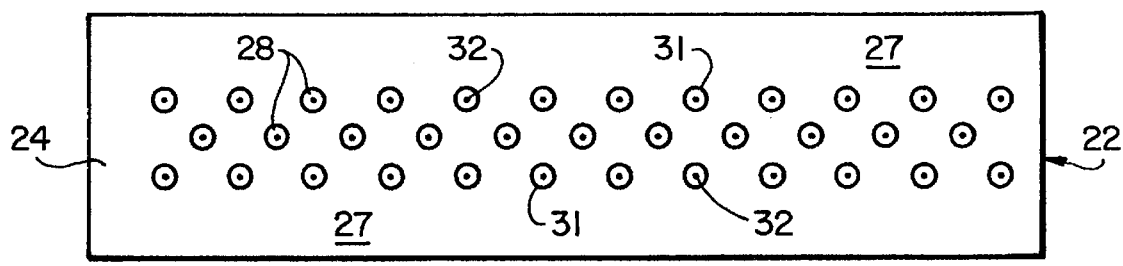
FIG_2
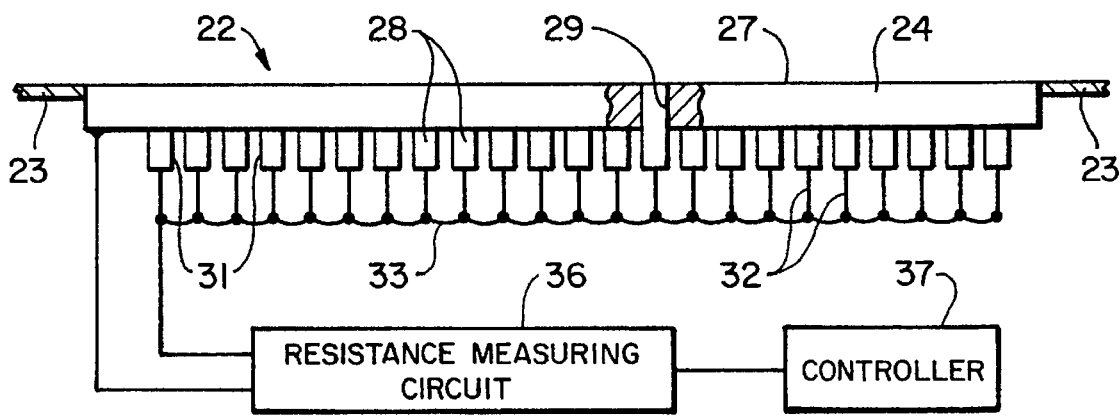
FIG_3

MOISTURE SENSOR FOR MICROWAVE CLOTHES DRYER

This invention pertains generally to microwave clothes dryers and, more particularly, to a moisture sensor for determining when the clothes in such a dryer are dry.

Microwave clothes dryers use high power levels to dry clothes quickly, yet gently. They are able to do so because the microwave energy primarily heats the water and not the fabrics as long as water is present in the dryer. However, when the water is fully evaporated, the microwave field strength increases significantly, and the microwaves begin to heat the fabric. If this continues, the fabric will soon be heated to the point of ignition. Although different fabrics may heat at different rates, eventually they will all be destroyed if heating continues after the moisture is gone.

Heretofore, there have been some attempts to sense when the water has been evaporated from a microwave dryer and to shut the dryer down at that point. In one such approach, the electric field strength within the drying chamber is monitored, and the power is shut off in response to a sudden increase. However, even though the increase is relatively significant when the water is gone, that increase is not sharp enough to provide reliable results, and the dryer may not be shut down in time to avoid burning of the clothes.

Another approach was to monitor the moisture content of the air exhausted from the dryer. That air tends to have a high relative humidity during most of the drying cycle and to drop sharply when drying is complete. However, that approach has not given reliable results either because the relative humidity of the exhaust is influenced heavily by the relatively humidity of the ambient air, and that varies widely from location to location. It is also affected by the heating of air coming into the dryer.

In conventional electric and gas powered dryers, moisture content has been monitored by making a direct measurement of the moisture in the clothes. That has been done by placing two parallel metal rails in the drying chamber and monitoring a small electric current applied to the rails to determine the moisture content of clothes in contact with the rails. That approach has produced satisfactory results in some conventional dryers. However, it cannot be used in microwave dryers because the rails would act as receiving antennas and conduct microwave energy out of the dryer. This would not only expose people near the dryers to microwave leakage, but would also damage the controls connected to the rails for shutting off the dryers.

It is in general an object of the invention to provide a new and improved system for detecting when clothes are dry in microwave clothes dryers.

Another object of the invention is to provide a system of the above character which overcomes the limitations and disadvantages of techniques previously employed.

These and other objects are achieved in accordance with the invention by providing a microwave clothes dryer with a moisture sensor having an array of short coaxial cables extending through an electrically conductive base plate which is grounded to the shielding structure of the dryer. The ends of the cables are flush with one side of the plate and are exposed for contact with clothes in the dryer chamber. Electrical resistance is monitored between the inner conductors and the plate to determine the dryness of clothes, and the dryer is shut down when the resistance reaches a predetermined level.

FIG. 1 is cross-sectional view, somewhat schematic, of one embodiment of a microwave clothes dryer incorporating the invention.

FIG. 2 is a top plan view of the moisture sensor in the embodiment of FIG. 1.

FIG. 3 is a side elevational view of the moisture sensor of FIG. 2.

In the drawings, the invention is illustrated in connection with a microwave dryer 11 having a rotating tumbler or drum 12 for holding clothes 13 to be dried within a chamber 14. The chamber is surrounded by a metal enclosure, or Faraday cage, 16 which prevents microwaves from escaping from the dryer. A door 17 in the front wall 18 of the enclosure provides access to the drum for insertion and removal of the clothes.

Microwave energy for evaporating water in the clothes is supplied to the chamber through a waveguide 19, and heated air is supplied through an air duct 21. As the air passes through the tumbling clothes, it picks up moisture which has been vaporized by the microwaves. The moisture laden air is removed from the chamber through an exhaust duct 21.

A moisture sensor 22 in contact with the clothes monitors the moisture content of the clothes to detect the drop in moisture content which occurs at the end of the drying cycle. That drop is utilized to shut down the dryer by terminating the delivery of microwave power to the chamber. The sensor is mounted on a bracket or shelf 23 which is attached to the front wall 18 of enclosure 16 and extends into the tumbler or drum, with the sensor being positioned to be contacted by the clothes tumbling within the drum.

The moisture sensor comprises a base plate 24 which is fabricated of an electrically conductive material, such as brass, and grounded electrically to the shielding enclosure or Faraday cage. In one embodiment, the plate is fabricated of brass and has a length of 6¼ inches, a width of 1½ inches and a thickness of ¼ inch.

A plurality of short lengths of coaxial cable 28 are mounted on the base plate. Each of the cables extends through an opening 29 which extends between the front and rear surfaces of the plate. The inner ends of the cables are flush with the front surface 27, and the inner ends of the conductors exposed to the chamber for contact with clothes tumbling therein. The outer conductors 31 extend approximately ¼ inch beyond the back surface of the plate and are bonded electrically to the plate by silver soldering to the walls of the openings. The outer ends of inner conductors 32 extend about ¼ inch beyond the outer ends of the outer conductors and are connected together electrically in parallel by a wire 33 silver soldered to their outer ends.

In the embodiment illustrated, thirty-five cables are provided, and they are arranged in an array consisting of three rows, with twelve cables in each of the outer rows and eleven cables in the inner row. In this particular embodiment, the cables are pieces of semi-rigid UG141A coaxial cable, the center-to-center spacing between the cables is approximately 0.33 inch, and the wire connecting the inner conductors together is a #18 AWG copper wire.

A resistance measuring circuit 36 is connected to the inner conductors 32 and to the base plate 24 to monitor the resistance of clothes in contact with the conductors and plate. That circuit provides an output signal to indicate the end of the drying cycle when the resistance increases to a predetermined level corresponding to the elimination of moisture from the clothes. The output signal is applied to a controller 37 which shuts down the microwave generator to terminate the delivery of microwave power to the chamber.

The invention has a number of important features and advantages. The sensor works reliably and shuts off the power at a point where the clothes are dry but not burned. With the coaxial cables, there is no leakage of microwaves from the dryer, nothing to act as an antenna, and no damage to the control circuitry It is apparent from the foregoing that a new and improved moisture sensor for microwave clothes dryers has been provided. While only certain presently preferred embodiments have been described in detail, as will be apparent to those familiar with the art, certain changes and modifications can be made without departing from the scope of the invention as defined by the following claims.

I claim:

1. In a moisture sensor for determining the dryness of clothes in the drying chamber of a microwave clothes dryer: an electrically conductive base plate, a plurality of coaxial cables extending through the base plate and terminating substantially flush with one side of the plate, the outer conductors of the cables being connected electrically to the plate and the inner conductors being exposed for contact with clothes in the chamber, and means for monitoring electrical resistance between the inner conductors and the base plate to determine the dryness of clothes in contact with the conductors and the plate.

2. The moisture sensor of claim 1 wherein the coaxial cables are arranged in an array.

3. The moisture sensor of claim 1 including means connecting the inner conductors electrically in parallel.

4. The moisture sensor of claim 3 wherein the inner conductors project from a second side of the base plate, and the means connecting the inner conductors electrically in parallel comprises an electrically conductive wire connected to the projecting ends of the conductors.

5. In a moisture sensor for determining the dryness of clothes in the drying chamber of a microwave clothes dryer: an electrically conductive base plate having an array of openings extending between opposite surfaces thereof, electrical conductors extending through the openings and ending flush with one of the surfaces for contact with clothes in the chamber, and means for monitoring electrical resistance between the conductors and the base plate to determine the dryness of clothes in contact with the conductors and the plate.

6. The moisture sensor of claim 5 wherein the conductors are inner conductors of coaxial cables which have outer conductors bonded electrically to the plate.

7. In a microwave clothes dryer: a chamber for holding clothes to be dried, means for introducing microwave energy into the chamber to evaporate moisture in the clothes, a Faraday cage for confining the microwave energy, an electrically conductive plate grounded to the cage and having an array of openings extending between opposite surfaces thereof, electrical conductors extending coaxially through the openings and ending flush with one of the surfaces for contact with clothes in the chamber, means for monitoring electrical resistance between the conductors and the base plate to determine the dryness of clothes in contact with the conductors and the plate, and means responsive to the monitored resistance for shutting off the dryer when the moisture content reaches a predetermined level.

8. The microwave clothes dryer of claim 7 wherein the conductors are inner conductors of coaxial cables which have outer conductors bonded electrically to the plate.

9. In a moisture sensor for determining the dryness of clothes in the drying chamber of a microwave clothes dryer: a base plate having an array of openings extending between front and back sides thereof, a short length of coaxial cable extending through each of the openings and terminating substantially flush with the front side of the plate, each length of coaxial cable having an outer conductor which projects a short distance from the back side of the plate and an inner conductor which projects a short distance beyond the outer conductor, means connecting the inner conductors together electrically in parallel on the back side of the plate, and means for monitoring electrical resistance between the inner and outer conductors to determine the dryness of clothes in contact with the conductors.

10. The moisture sensor of claim 9 wherein the base plate is electrically conductive, and the outer conductors are connected electrically to the base plate.

* * * * *